United States Patent [19]

DeMarinis et al.

[11] 3,943,127

[45] Mar. 9, 1976

[54] 7-TRIFLUOROMETHYLSUL-FINYLACETAMIDO CEPHALOSPORINS

[75] Inventors: Robert M. DeMarinis, King of Prussia; John R. E. Hoover, Glenside, both of Pa.

[73] Assignee: SmithKline Corporation, Philadelphia, Pa.

[22] Filed: Jan. 20, 1975

[21] Appl. No.: 542,336

Related U.S. Application Data

[62] Division of Ser. No. 371,081, June 18, 1973, Pat. No. 3,880,848.

[52] U.S. Cl. ........... 260/243 C; 260/526 S; 424/246
[51] Int. Cl.² ........................................ C07D 501/28
[58] Field of Search ................................ 260/243 C

[56] References Cited
UNITED STATES PATENTS

| | | | |
|---|---|---|---|
| 3,297,692 | 1/1967 | Flynn | 260/243 C |
| 3,335,136 | 8/1967 | Flynn | 260/243 C |
| 3,382,238 | 7/1968 | Dolfini | 260/243 C |
| 3,828,037 | 8/1974 | DeMarinis et al. | 260/243 C |

*Primary Examiner*—Donald G. Daus
*Assistant Examiner*—Diana G. Rivers
*Attorney, Agent, or Firm*—Janice E. Williams; Alan D. Lourie; William H. Edgerton

[57] ABSTRACT

Cephalosporin compounds having a trifluoromethylsulfinylacetamido group at the 7-position and various groups at the 3-position are prepared by acylation of a 7-aminocephalosporanic acid. The compounds have antibacterial activity.

2 Claims, No Drawings

7-TRIFLUOROMETHYLSULFINYLACETAMIDO CEPHALOSPORINS

This is a divisional application Ser. No. 371,081 filed June 18, 1973, now U.S. Pat. No. 3,880,848.

This invention relates to cephalosporin compounds which have antibacterial activity. In particular, the invention relates to compounds having a trifluoromethylsulfinylacetamido substituent at position 7 of the cephem nucleus.

The compounds of this invention are represented by the following structural formula:

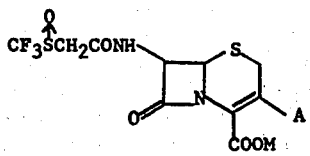

in which:

M is hydrogen or an alkali metal or ammonium cation;

A is hydrogen, methyl, acetoxymethyl, pyridiniummethyl, $CH_2SHet$, $CH_2SR'$ or $CH_2OR'$, where $R'$ is hydrogen or alkyl of from one to four carbon atoms; and Het is a five or six membered heterocyclic group containing carbon and one to four atoms selected from the group consisting of N, O and S, each such group being unsubstituted or substituted with from one to two groups selected from lower alkyl, alkoxyalkyl, and trifluoromethyl, each alkyl or alkoxy group having from one to four carbon atoms, or an N-oxide thereof.

Preferred compounds are those where A is acetoxymethyl or $CH_2SHet$. Particularly preferred as those compounds where Het is unsubstituted or methyl substituted 1,2,3-triazolyl, 1,2,4-triazolyl, 1,2,3,4-tetrazolyl, oxazolyl, thiazolyl, 1,3,4-oxadiazolyl, 1,3,4-thiadiazolyl, or 1,2,4-thiadiazolyl.

Included within the scope of this invention are the pharmaceutically acceptable salts that are formed by reaction of the cephalosporanic acid with a pharmaceutically acceptable base.

Cephalosporins with a wide variety of acyl groups at position 7 of the cephem nucleus have been disclosed in the prior art, including many 7-alkylmercaptoacetamidocephalosporanic acid derivatives (U.S. Pat. Nos. 3,573,298, 3,297,692 and others). 7-Substituted alkylsulfinylacetamidocephalosporanic acids variously substituted at position 3 (but not with $CH_2SHet$) are described in U.S. Pat. No. 3,382,238 and German Pat. No. 2,000,878. Our own copending application Serial No. 273,571, filed July 20, 1972, now U.S. Pat. No. 3,828,037, discloses 7-trifluoromethylmercaptoacetamidocephalosporins. However, no cephalosporins with a trifluoromethylsulfinyl group in the 7-acyl substituent are known.

The compounds of this invention are prepared by acylation of the appropriately substituted 7-aminocephalosporanic acid with trifluoromethylsulfinylacetic acid. The carboxyl group of the acylating agent may be activated by one of the methods known in the art such as the mixed anhydride, acid halide, or activated ester. In addition, acylation of esters of the cephalosporin nucleus may be done by use of a coupling reagent such as dicyclohexylcarbodiimide.

Following the acylation, the protective groups can be removed with an acid such as trifluoroacetic acid.

The compounds are also prepared by displacement of a 7-acylated 3-acetoxymethylcephalosporin with a mercaptoheterocycle in an aqueous, slightly basic medium.

Trifluoromethylsulfinylacetic acid is prepared by hydrogen peroxide oxidation of trifluoromethylmercaptoacetic acid according to known procedures [Zh. Obshch. Khim. 35, 9, 1628 (1965)].

The compounds of this invention have antibacterial activity against both Gram-positive and Gram-negative organisms. Minimum inhibitory concentrations (MIC's) ranged from 0.1 to >200 μg/ml in in vitro testing. These results are shown below for 7-trifluoromethylsulfinylacetamido-3-acetoxymethyl-3-cephem-4-carboxylic acid (I) and 7-tri-fluoromethylsulfinylacetamido-3-(1-methyl-1,2,3,4-tetrazol-5-ylthiomethyl)-3-cephem-4-carboxylic acid (II). When administered in vivo (s.c.), compound I showed an $ED_{50}$ of 29 mg/kg against E. coli and >200 mg/kg against Klebs. pneumo. The $ED_{50}$ for compound II against E coli was 4.6–22 mg/kg; against Klebs. pneumo. it was 50–56 mg/kg.

TABLE 1

| Bacteria | MIC (mg/ml) I | II |
| --- | --- | --- |
| S. aureus HH 127 | 1.6 | 0.8 |
| S. aureus SK 23390 | 1.6 | 0.8 |
| Strep. pyog. C203 | 0.2 | 0.1 |
| Strep. faecalis HH 34358 | 100 | 100 |
| E. coli SK 12140 | 6.3 | 0.8 |
| E. coli HH 33779 | 12.5 | 1.6 |
| Kleb. pneumo. SK 4200 | 3.1 | 0.8 |
| Kleb. pneumo. SK 1200 | 3.1 | 0.8 |
| Pseudomonas sp. HH 63 | > 200 | > 200 |
| Salmonella | 3.1 | 0.4 |
| Shigella | 6.3 | 0.4 |
| Entero. aerogenes | 50 | 1.6 |
| Serratia marc. ATCC 13880 | > 200 | > 200 |
| S. villaluz SK 70390 | 100 | 50 |
| Entero. cloaca HH 31254 | 12.5 | — |

These compounds are formulated and administered by injection in doses of 250–500 mg in the same manner as other cephalosporins. The precise dosages are dependent upon the age and weight of the subject and on the nature of the infection being treated. Determination of dosages is within the skill of the art.

The following examples illustrate the invention, but are not to be construed as limiting the scope thereof. Temperatures are in degrees Centigrade unless otherwise stated.

EXAMPLE 1

7-Trifluoromethylsulfinylacetamido-3-acetoxymethyl-3-cephem-4-carboxylic acid

To a solution of 0.264 g (1.5 mmol) of trifluoromethylsulfinylacetic acid and 0.592 g (1.5 mmol) of 7-ACA t-butyl ester in 10 ml of tetrahydrofuran was added 0.309 g (1.5 mmol) of dicyclohexylcarbodiimide. After stirring at 25° for 2 hr., the reaction mixture was refrigerated overnight. The solution was then filtered and the filtrate was concentrated to yield a gum that was dissolved in 10 ml of 100 percent trifluoroacetic acid and allowed to stand at room temperature for 15 minutes. Concentration in vacuo gave 7-trifluoromethylsulfinylacetamido-3-acetoxymethyl-3-cephem-4-carboxylic acid as a gum which was then dissolved in 50 ml of ethyl acetate. The solution was filtered and to the filtrate was added with stirring 1.5 ml of a 30 percent solution of sodium 2-ethylhexanoate in isopropanol. Dropwise addition of the resultant solution to 200 ml of pet ether caused precipitation of the sodium salt (0.515 g, 73 percent) which was collected and purified by solution in 5 ml of acetonitrile and addition of this solution to 100 ml of rapidly stirred ether. The preciptate was collected, washed with ether and dried in vacuo to give 0.370 g of pure salt.

$C_{13}H_{12}F_3N_2O_7S_2 \cdot Na.1\ H_2O.1\ CF_3CO_2H$ (584.424)

|   | Theory | Found |
|---|--------|-------|
| C | 30.91  | 30.58 |
| H | 2.58   | 2.36  |
| N | 4.79   | 4.73  |
| S | 10.96  | 11.21 |
| F | 19.50  | 17.13 |

EXAMPLE 2

7-Amino-3-(1-methyl-1,2,3,4-tetrazol-5-ylthiomethyl)-3-cephem-4-carboxylic acid

To a suspension of 27.2 g (0.1 mol) of 7-ACA in 200 ml of water and 100 ml of acetone was added a solution of 18.9 g of sodium bicarbonate in 200 ml of water. The resultant solution was warmed on a steam bath and a solution of 14.5 g (0.125 mol) of 1-methyl-5-mercapto-1,2,3,4-tetrazole in 200 ml of acetone was added. The reaction mixture was refluxed for 3.5 hr. while maintaining the pH at 7.4–8.0 by addition of 5 percent sodium bicarbonate. Acidification of the cooled reaction mixture to pH 3.5 with 6N hydrochloric acid resulted in precipitation of 7-amino-3-(1-methyl-1,2,3,4-tetrazol-5-ylthiomethyl)-3-cephem-4-carboxylic acid, which was collected, washed with water and air dried (16 g, 49 percent).

EXAMPLE 3

7-Trifluoromethylsulfinylacetamido-3-(1-methyl-1,2,3,4-tetrazol-5-ylthiomethyl)-3-cephem-4-carboxylic acid To a solution of 1.54 g (0.004 mol) of 7-amino-3-(1-methyl-1,2,3,4-tetrazol-5-ylthiomethyl)-3-cephem-4-carboxylic acid, t-butyl ester and 0.825 g (0.004 mol) of dicyclohexylcarbodiimide in 50 ml of benzene was added 0.704 g (0.004 mol) of trifluoromethylsulfinylacetic acid. The reaction mixture was stirred at 25° for 2 hr., then it was filtered and adsorbed onto 4 g of silica gel. Chromatography on 100 g of silica gel with 50:50 benzene-ethyl acetate gave 1.55 g (69 percent) of 7-trifluoromethylsulfinylacetamido-3-(1-methyl-1,2,3,4-tetrazol-5-ylthiomethyl)-3-cephem-4-carboxylic acid, t-butyl ester as a white foam. The ester was dissolved in 9 ml of trifluoroacetic acid and stirred at 25° for 5 minutes, then added dropwise to 200 ml of ether. The precipitate was collected, dissolved in 5 percent sodium bicarbonate and the solution was diluted to 150 ml. After extraction with ethyl acetate the aqueous phase was acidified to pH 1.5 and extracted thrice more with ethyl acetate. The combined extracts were dried (MgSO₄) and concentrated to 35 ml, to which residue (the free acid) was added a solution of 1.5 of 30 percent sodium 2-ethylhexanoate in isopropanol followed by 200 ml of ether. The precipitated salt was collected, reprecipitated from methanol-ether and dried in vacuo to give 0.680 g of product.

$C_{13}H_{12}F_3N_6O_5S_3 \cdot Na.1/2H_2O$ (517.484)

|   | Theory | Found |
|---|--------|-------|
| C | 30.18  | 30.32 |
| H | 2.53   | 2.70  |
| N | 16.24  | 15.23 |

EXAMPLE 4

7-Trifluoromethylsulfinylacetamido-3-(1,3,4-thiadiazol-2-ylthiomethyl)-3-cephem-4-carboxylic acid To a solution of 3.1 g (0.009 mol) of 7-amino-3-(1,3,4-thiadiazol-2-ylthiomethyl)-3-cephem-4-carboxylic acid in 60 ml of 3% aqueous sodium bicarbonate is added 60 ml of acetone. The solution is cooled to −15° and 1.94 g (0.010 mol) of trifluoromethylsulfinylacetyl chloride in 20 ml of acetone is added over a 10-minute period. The reaction mixture is stirred at −15° for 30 minutes while maintaining the pH at 7.6–8.0 by addition of 10 percent sodium hydroxide, then at 25° for 1 hour. The reaction mixture is extracted once with ether and the aqueous phase is acidified to pH 2.5 with dilute hydrochloric acid and extracted with ethyl acetate. The organic extracts are dried (MgSO₄) and concentrated in vacuo to give the title compound.

EXAMPLE 5

When either an equivalent amount of a 7-amino-3-heterocyclicthiomethyl-3-cephem-4-carboxylic acid (prepared by the procedure of Example 2) listed below is substituted into the procedure of Example 4 for 7-amino-3-(1,3,4-thiadiazol-2-ylthiomethyl)-3-cephem-4-carboxylic acid or its t-butyl ester is substituted into the procedure of Example 3 for 7-amino-3-(1-methyl-1,2,3,4-tetrazol-5-ylthiomethyl)-3-cephem-4-carboxylic acid, t-butyl ester, the appropriate 7-trifluoromethylsulfinylacetamido-3-heterocyclicthiomethyl-3-cephem-4-carboxylic acid is obtained.

7-amino-3-(5-methyl-1,3,4-thiadiazol-2-ylthiomethyl)-3-cephem-4-carboxylic acid 7-amino-3-(5-ethyl-1,3,4-thiadiazol-2-ylthiomethyl)-3-cephem-4-carboxylic acid 7-amino-3-(5-trifluoromethyl-1,3,4-thiadiazol-2-ylthiomethyl)-3-cephem-4-carboxylic acid 7-amino-3-(5-n-butyl-1,3,4-thiadiazol-2-ylthiomethyl)-3-cephem-4-carboxylic acid 7-amino-3-(1,2,4-thiadiazol-5-ylthiomethyl)-3-cephem-4-carboxylic acid 7-amino-3-(3-methyl-1,2,4-thiadiazol-5-ylthiomethyl)-3-cephem-4-carboxylic acid 7-amino-3-(3-ethyl-1,2,4-thiadiazol-5-ylthiomethyl)-3-cephem-4-carboxylic acid 7-amino-3-(thiazol-5-ylthiomethyl)-3-cephem-4-carboxylic acid 7-amino-3-(2-methylthiazol-5-ylthiomethyl)-3-cephem-4-carboxylic acid 7-amino-3-(4-methylthiazol-5-ylthiomethyl)-3-cephem-4-carboxylic acid 7-amino-3-(2,4-dimethylthiazol-5-ylthiomethyl)-3-cephem-4-carboxylic acid 7-amino-3-(2-ethylthiazol-5-ylthiomethyl)-3-cephem-4-carboxylic acid 7-amino-3-(4-ethylthiazol-5-ylthiomethyl)-3-cephem-4-carboxylic acid 7-amino-3-(2,4-diethylthiazol-5-ylthiomethyl)-3-cephem-4-carboxylic acid 7-amino-3-(1,3,4-oxadiazol-2-ylthiomethyl)-3-cephem-4-carboxylic acid 7-amino-3-(5-methyl-1,3,4-oxadiazol-2-ylthiomethyl)-3-cephem-4-carboxylic acid 7-amino-3-(oxazol-5-ylthiomethyl)-3-cephem-4-carboxylic acid 7-amino-3-(2-methyloxazol-5-ylthiomethyl)3-cephem-4-carboxylic acid 7-amino-3-(4-methyloxazol-5-ylthiomethyl)-3-cephem-4-carboxylic acid 7-amino-3-(1,2,4-dimethyloxazol-5-ylthiomethyl)-3-cephem-4-carboxylic acid 7-amino-3-(2-ethyloxazol-5-ylthiomethyl)-3-cephem-4-carboxylic acid 7-amino-3-(4-ethyloxazol-5-ylthiomethyl)-3-cephem-4-carboxylic acid 7-amino-3-(2,4-dimethyloxazol-5-ylthiomethyl)-3-cephem-4-carboxylic acid 7-amino-3-(1,2,3,4-tetrazol-5-ylthiomethyl)-3-cephem-4-carboxylic acid 7-amino-3-(1-ethyl-1,2,3,4-tetrazol-5-ylthiomethyl)-3-cephem-4-carboxylic acid 7-amino-3-(1-methoxymethyl-1,2,3,4-tetrazol-5-ylthiomethyl)-3-cephem-4-carboxylic acid 7-amino-3-(1,2,4-triazol-3-ylthiomethyl)-3-cephem-4-carboxylic acid 7-amino-3-(4-methyl-1,2,4-triazol-3-ylthiomethyl)-3-cephem-4-carboxylic acid 7-amino-3-(5-methyl-1,2,4-triazol-3-ylthiomethyl)-3-cephem-4-carboxylic acid 7-amino-3-(1-methyl-1,2,4-triazol-5-ylthiomethyl)-3-cephem-4-carboxylic acid 7-amino-3-(1-methyl-1,2,4-triazol-3-ylthiomethyl)-3-cephem-4-carboxylic acid 7-amino-3-(1,5-dimethyl-1,2,4-triazol-3-ylthiomethyl)-3-cephem-4-carboxylic acid 7-amino-3-(1,3-dimethyl-1,2,4-triazol-5-ylthiomethyl)-3-cephem-4-carboxylic acid 7-amino-3-(4,5-dimethyl-1,2,4-triazol-3-ylthiomethyl)-3-cephem-4-carboxylic acid 7-amino-3-(4-ethyl-1,2,4-triazol-3-ylthiomethyl)-3-cephem-4-carboxylic acid 7-amino-3-(5-ethyl-1,2,4-triazol-3-ylthiomethyl)-3-cephem-4-carboxylic acid 7-amino-3-(1-ethyl-1,2,4-triazol-5-ylthiomethyl)-3-cephem-4-carboxylic acid 7-amino-3-(1-ethyl-1,2,4-triazol-3-ylthiomethyl)-3-cephem-4-carboxylic acid 7-amino-3-(1,5-diethyl-1,2,4-triazol-3-ylthiomethyl)-3-cephem-4-carboxylic acid 7-amino-3-(4,5-diethyl-1,2,4-triazol-3-ylthiomethyl)-3-cephem-4-carboxylic acid 7-amino-3-(1,3-diethyl-1,2,4-triazol-5-ylthiomethyl)-3-cephem-4-carboxylic acid 7-amino-3-(4-methoxymethyl-1,2,4-triazol-3-ylthiomethyl)-3-cephem-4-carboxylic acid 7-amino-3-(4-methyl-5-trifluoromethyl-1,2,4-triazol-3-ylthiomethyl)-3-cephem-4-carboxylic acid 7-amino-3-(4-allyl-1,2,4-triazol-3-ylthiomethyl)-3-cephem-4-carboxylic acid 7-amino-3-(1,2,3-triazol-4-ylthiomethyl)-3-cephem-4-carboxylic acid 7-amino-3-(3-methyl-1,2,3-triazol-4-ylthiomethyl)-3-cephem-4-carboxylic acid 7-amino-3-(5-methyl-1,2,3-triazol-4-ylthiomethyl)-3-cephem-4-carboxylic acid 7-amino-3-(3,5-dimethyl-1,2,3-triazol-4-ylthiomethyl)-3-cephem-4-carboxylic acid 7-amino-3-(3-ethyl-1,2,3-triazol-4-ylthiomethyl)-3-cephem-4-carboxylic acid 7-amino-3-(5-ethyl-1,2,3-triazol-4-ylthiomethyl)-3-cephem-4-carboxylic acid 7-amino-3-(3,5-diethyl-1,2,3-triazol-4-ylthiomethyl)-3-cephem-4-carboxylic acid 7-amino-3-(3-methoxymethyl-1,2,3-triazol-4-ylthiomethyl-3-cephem-4-carboxylic acid 7-amino-3-(4-pyridylthiomethyl)-3-cephem-4-carboxylic acid 7-amino-3-(3-pyridylthiomethyl)-3-cephem-4-carboxylic acid 7-amino-3-(4-pyrimidylthiomethyl)-3-cephem-4-carboxylic acid 7-amino-3-(2-pyrazinylthiomethyl)-3-cephem-4-carboxylic acid 7-amino-3-(2-N-oxopyridylthiomethyl)-3-cephem-4-carboxylic acid

EXAMPLE 6

7-Trifluoromethylsulfinylacetamido-3-methyl-3-cephem-4-carboxylic acid

When an equivalent amount of 7-amino-3-methyl-3-cephem-4-carboxylic acid is substituted for 7-ACA, t-butyl ester in the procedure of Example 1, 7-trifluoromethylsulfinylacetamido-3-methyl-3-cephem-4-carboxylic acid is obtained.

EXAMPLE 7

7-Trifluoromethylsulfinylacetamido-3-(1-pyridiniummethyl)-3-cephem-4-carboxylic acid To a solution of 4.5 g (0.01 mol) of 7-trifluoromethylsulfinylacetamidocephalosporanic acid sodium salt in 25 ml of water is added 2.23 g (0.023 mol) of potassium thiocyanate and 2.2 ml (0.028 mol) of pyridine. The reaction mixture is heated at 65°–70° for 7 hr. After cooling, the mixture is diluted with 100 ml of water and the aqueous solution is chromatographed on a column of crosslinked polystyrene polymer (Amberlite XAD-2). The inorganic salts are eluted with water, then the product is eluted with 95 percent ethanol. Evaporation of the eluent gives the title compound.

EXAMPLE 8

7-Trifluoromethylsulfinylacetamido-3-methylthiomethyl-3-cephem-4-carboxylic acid Acylation of 7-amino-3-methylthiomethyl-3-cephem-4-carboxylic acid (Belgian Pat. No. 743,754), t-butyl ester with trifluoromethylsulfinylacetic acid according to the procedure of Example 1 gives the title compound.

EXAMPLE 9

7-Trifluoromethylsulfinylacetamido-3-methoxymethyl-3-cephem-4-carboxylic acid

Acylation of 7-amino-3-methoxymethyl-3-cephem-4-carboxylic acid [*J. Med. Chem.*, 14, 113 (1971)], t-butyl ester with trifluoromethylsulfinylacetic acid according to the procedure of Example 1 gives the title compound.

EXAMPLE 10

7-Trifluoromethylsulfinylacetamido-3-cephem-4-carboxylic acid

A solution of 0.78 g (2 mmol) of benzhydryl 7-amino-3-cephem-4-carboxylate (South African Pat. No. 71/06719), 0.35 g (2 mmol) of trifluoromethylsulfinylacetic acid and 0.4 g (2 mmol) of dicyclohexylcarbodiimide in dry tetrahydrofuran (15 ml) is stirred at room temperature overnight. The precipitate is collected and washed with tetrahydrofuran and the combined filtrate and washings are evaporated in vacuo. The residue is treated with a cold solution of trifluoroacetic acid (10 ml) and anisole (0.5 g) for 15 minutes and then concentrated in vacuo. The residue is dissolved in ethyl acetate and treated with 5 percent aqueous sodium bicarbonate. The aqueous phase is adjusted to pH 2 and the precipitated product is collected and dried.

EXAMPLE 11

An injectable pharmaceutical composition is formed by adding sterile water or sterile saline solution (2 ml) to 500 mg of 7-trifluoromethylsulfinylacetamido-3-(1-methyl-1,2,3,4-tetrazol-5-ylthiomethyl)-3-cephem-4-carboxylic acid, sodium salt.

Pharmaceutical compositions of the other antibacterial compounds described by Formula I or disclosed in the above examples may be formulated in a similar manner.

We claim:

1. A compound of the formula:

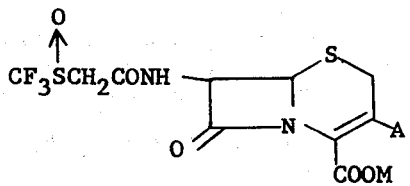

in which:

M is hydrogen or an alkali metal or ammonium cation; and

A is acetoxymethyl, methyl or pyridiniummethyl [, pyridiniummethyl, CH$_2$SHet, CH$_2$SR' or CH$_2$OR', where R' is hydrogen or alkyl of from one to four carbon atoms; and Het is a five or six membered heterocyclic group containing carbon and one to four atoms selected from the group consisting of N, O and S, each such group being unsubstituted or substituted with from one to two groups selected from lower alkyl, alkoxyalkyl, and trifluoromethyl, each alkyl or alkoxy having from one to four carbon atoms, or an N-oxide thereof].

2. A compound as claimed in claim 1, being the compound 7-trifluoromethylsulfinylacetamido-3-acetoxymethyl-3-cephem-4-carboxylic acid.

* * * * *

UNITED STATES PATENT OFFICE
CERTIFICATE OF CORRECTION

PATENT NO. : 3,943,127
DATED : March 9, 1976
INVENTOR(S) : Robert M. DeMarinis and John R. E. Hoover It is certified that error appears in the above-identified patent and that said Letters Patent are hereby corrected as shown below:

Column 1, line 35    "as" should read  -- are --

Column 2, line 15    "7-tri-fluoromethyl-" should read

-- 7-trifluoromethyl- --

Column 3, line 64    "1.5" should read  -- 1.5 g --

Claim 1 should read as follows:

1. A compound of the formula:

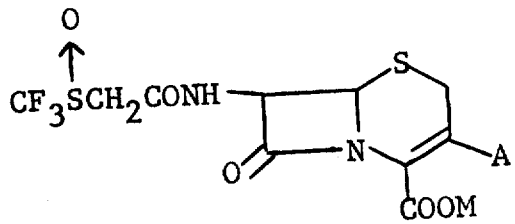

in which:

M is hydrogen or an alkali metal or ammonium cation; and

A is acetoxymethyl, methyl or pyridinium-methyl.

Signed and Sealed this

Twentieth Day of July 1976

[SEAL]

Attest:

RUTH C. MASON
Attesting Officer

C. MARSHALL DANN
Commissioner of Patents and Trademarks